US008344149B2

(12) United States Patent
Pathi et al.

(10) Patent No.: US 8,344,149 B2
(45) Date of Patent: Jan. 1, 2013

(54) CRYSTALLINE FORM OF BENZOTHIOPHENE COMPOUND AND PROCESS FOR PREPARATION THEREOF

(75) Inventors: Srinivas Laxminarayan Pathi, Bangalore (IN); Rajendra Narayanrao Kankan, Mumbai (IN); Dharmaraj Ramachandra Rao, Thane (IN)

(73) Assignee: Cipla Limited, Mumbai (IN)

( * ) Notice: Subject to any disclaimer, the term of this patent is extended or adjusted under 35 U.S.C. 154(b) by 575 days.

(21) Appl. No.: 12/445,385

(22) PCT Filed: Oct. 17, 2007

(86) PCT No.: PCT/GB2007/003943
§ 371 (c)(1),
(2), (4) Date: Apr. 1, 2010

(87) PCT Pub. No.: WO2008/047105
PCT Pub. Date: Apr. 24, 2008

(65) Prior Publication Data
US 2011/0009450 A1 Jan. 13, 2011

(30) Foreign Application Priority Data
Oct. 17, 2006 (IN) .......................... 1718/MUM/2006

(51) Int. Cl.
*C07D 409/00* (2006.01)
*A61K 31/445* (2006.01)
(52) U.S. Cl. ....................................... 546/202; 514/324
(58) Field of Classification Search .................. 546/202; 514/324
See application file for complete search history.

(56) References Cited

U.S. PATENT DOCUMENTS

| 4,133,814 A | 1/1979 | Jones et al. |
| 4,358,593 A | 11/1982 | Jones et al. |
| 4,380,635 A | 4/1983 | Peters |
| 4,418,068 A | 11/1983 | Jones |
| 5,523,416 A | 6/1996 | Alt |
| 5,606,075 A | 2/1997 | Hoard et al. |
| 5,606,076 A | 2/1997 | Aikins et al. |
| 5,731,327 A | 3/1998 | Luke |
| 2002/0173645 A1 | 11/2002 | Luke |

FOREIGN PATENT DOCUMENTS

| EP | 0062503 A1 | 10/1982 |
| EP | 0693488 A1 | 1/1996 |
| EP | 0842930 A1 | 5/1998 |
| EP | 0875511 A1 | 11/1998 |
| WO | 9609045 A1 | 3/1996 |
| WO | 9735571 A1 | 10/1997 |
| WO | 9808513 A1 | 3/1998 |
| WO | 9848792 | 11/1998 |
| WO | 9848793 A1 | 11/1998 |
| WO | 9849156 A1 | 11/1998 |
| WO | 2004/029046 A2 | 4/2004 |
| WO | 2005003116 A1 | 1/2005 |
| WO | 2008047105 A1 | 4/2008 |

OTHER PUBLICATIONS

Caira, Mino R., "Crystalline polymorphism of organic compounds," Topics in Current Chemistry, 1998, pp. 163-208, vol. 198, Springer Verlag Berlin Heidelberg, XP-001156954.
Foreign communication from the priority application—International Search Report and Written Opinion, PCT/GB2007/003943, Jan. 23, 2008, 15 pages.
Foreign communication from the priority application—International Preliminary Report on Patentability, PCT/GB2007/003943, Apr. 30, 2009, 9 pages.
Foreign communication from a related application—Examination Report, GB0906857.8, Nov. 9, 2010, 3 pages.

*Primary Examiner* — Janet Andres
*Assistant Examiner* — John Mabry
(74) *Attorney, Agent, or Firm* — Conley Rose, P.C.; Rodney B. Carroll

(57) ABSTRACT

Crystalline raloxifene hydrochloride in hydrated form, particularly the monohydrate, processes for its preparation, pharmaceutical compositions comprising it and uses thereof.

17 Claims, 3 Drawing Sheets

CRYSTALLINE FORM OF BENZOTHIOPHENE COMPOUND AND PROCESS FOR PREPARATION THEREOF

TECHNICAL FIELD OF INVENTION

The present invention relates to a novel crystalline polymorph of raloxifene hydrochloride, chemically termed as [6-hydroxy-2-(4-hydroxyphenyl)-benzothiophen-3-yl]-[4-[2-(1-piperidyl)ethoxy]phenyl]-methanone hydrochloride and process for preparation thereof. Further, the invention also relates to pharmaceutical compositions comprising crystalline raloxifene hydrochloride used for osteoporosis in postmenopausal women and the use of the crystalline polymorphic form in making the compositions.

BACKGROUND AND PRIOR ART

Raloxifene hydrochloride is a selective estrogen receptor modulator (SERM) that belongs to the benzothiophene class of compounds and it is useful for the prevention of osteoporosis in postmenopausal women. Raloxifene hydrochloride is represented by the following structure.

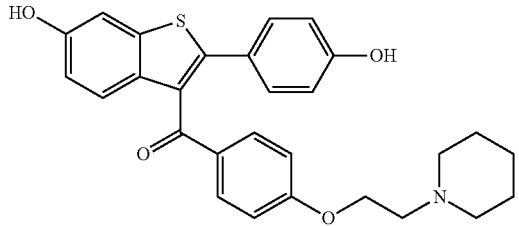 [SMILES: O=C(c1ccc(OCCN2CCCCC2)cc1)c1c(-c2ccc(O)cc2)sc2cc(O)ccc12]

Raloxifene base was disclosed in U.S. Pat. No. 4,133,814. Other methods of preparing raloxifene base are disclosed in patents WO9848792, U.S. Pat. No. 4,380,635.

Raloxifene hydrochloride was first disclosed in U.S. Pat. No. 4,418,068. This patent does not disclose any polymorphic forms of raloxifene hydrochloride. Other methods of preparation of raloxifene hydrochloride are disclosed in WO2005003116, EP0875511, U.S. Pat. No. 5,606,076, U.S. Pat. No. 5,606,075, EP842930, WO9848793, WO9849156, EP0693488 and U.S. Pat. No. 5,523,416.

U.S. Pat. No. 4,358,593 discloses a process for the preparation of raloxifene and its salts.

WO9609045 discloses non-solvated, crystalline raloxifene hydrochloride characterized by XRD, DSC and IR.

WO9735571 discloses raloxifene, salts and solvates thereof, characterized by XRD. Further the above patent also discloses pharmaceutical compositions comprising the compounds and methods of treatment involving the use of such compounds.

WO2004029046 discloses raloxifene L-lactate hemihydrate, DL-lactate hemihydrate and raloxifene sulphate 2-propanol solvate characterized by XRD and DSC. Processes for their preparation and pharmaceutical compositions containing these compounds are also disclosed in this patent for the treatment of cancer, osteoporosis or for inhibiting cartilage degradation.

US20020173645 discloses a series of crystalline polymorphic forms of raloxifene hydrochloride namely Form I (a 1,2-dichloroethane solvate), Form –II (another 1,2-dichloroethane solvate), Form III (a chlorobenzene solvate), Form IV (a chloroform solvate) and a nonsolvated crystalline form, characterized by XRD and the processes for preparation thereof.

WO9808513 discloses a process for preparation of an amorphous form of raloxifene hydrochloride, which comprises preparing a solution of crystalline form of raloxifene hydrochloride in a suitable solvent, and then spray drying the solution to recover an amorphous form.

SUMMARY OF THE INVENTION

According to a first aspect of the present invention, there is provided crystalline raloxifene hydrochloride in hydrated form. In an embodiment, the hydrated form has the formula

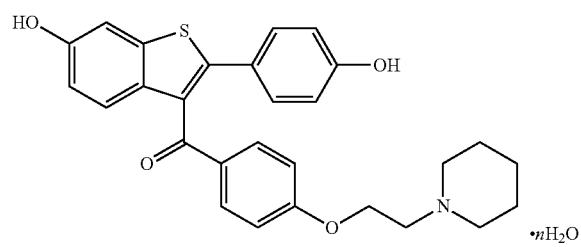

wherein n is an integer of 1 to 5, or a reciprocal of integers 2 to 5. Preferably, n is 1, i.e. crystalline raloxifene hydrochloride monohydrate.

Crystalline raloxifene hydrochloride monohydrate may be characterised by having an XRPD with peaks at 18.3 and 20.3° 2θ±0.2° 2θ. The XRPD may have further peaks at 20.9, 22.0, 22.3, 25.8 and 30.2° 2θ±0.2° 2θ. In an embodiment, crystalline raloxifene hydrochloride monohydrate has an XRPD as shown in FIG. 1.

Crystalline raloxifene hydrochloride monohydrate may be characterised by having a differential scanning calorimetric thermogram exhibiting significant endo peaks at 144° C. and 263° C. In an embodiment, crystalline raloxifene hydrochloride monohydrate has a differential scanning calorimetric thermogram as shown in FIG. 2.

Crystalline raloxifene hydrochloride monohydrate may also be characterised by having an infrared spectrum with peaks indicated around 3506, 3378, 3251, 2952, 2669, 1572, 1490, 1438, 1366, 1143, 966, 816, 572, 526 and 507 cm$^{-1}$. In an embodiment, crystalline raloxifene hydrochloride monohydrate has an infrared spectrum as shown in FIG. 3.

In another embodiment, crystalline raloxifene hydrochloride monohydrate is characterised as having a water content ranging from 3 to 4%.

According to another aspect of the present invention, there is provided a process for the preparation of crystalline raloxifene hydrochloride monohydrate comprising the steps of:
a) dissolving crystalline raloxifene hydrochloride in a C1-C4 alkanol or mixtures thereof, water and a water miscible solvent and optionally a colour removing agent;
b) optionally charcoaling and filtering the solution;
c) adjusting the pH of the solution to acidic;
d) isolating the solid obtained from step c); and
e) drying the compound to afford the crystalline polymorph of raloxifene hydrochloride monohydrate.

In an embodiment, step a) is carried out at a temperature ranging from 40 to 90° C., preferably 60 to 65° C., typically for a period of time ranging from 30 minutes to 2 hours.

In an embodiment, the C1 to C4 alkanol used in step a) is selected from the group consisting of methanol, isopropyl alcohol, ethanol or butanol. Preferably, the C1 to C4 alkanol is methanol.

The water miscible solvent may be selected from the group consisting of dimethylormamide, dimethylacetamide, tetrahydrofuran or dimethylsulfoxide, preferably dimethylformamide.

Sodium metabisulphite, dry or in the form of an aqueous solution, may be added to the solution in step a). Preferably, it is added as a dilute aqueous solution, for example 0.5 g of sodium metabisulphite dissolved in 5 ml of water.

If the charcoaling step in step b) is carried out, it may be carried out for a period of time ranging from 1 to 2 hours.

The pH in step c) may be adjusted with an acid to a value ranging from 1.5 to 2. The acid may be hydrochloric acid. The acid may be in the form of a gas or as an aqueous solution, preferably an aqueous solution.

Following step c), the reaction mass may be cooled, typically to a temperature ranging from 40 to 65° C., preferably to a temperature ranging from 20 to 40° C., more preferably to a temperature ranging from 20 to 35° C. The reaction mass may be stirred during step c) to complete crystallisation.

Prior to step d), the volume of the reaction mass may be reduced by concentrating under vacuum. The concentration may be reduced to a volume ranging from 10 to 15% volume, suitably to 11%.

The isolation in step d) may be carried out by filtering, decanting or centrifuging.

The drying in step e) may be carried out at a temperature ranging from 40 to 100° C.

The starting material in step a), crystalline raloxifene hydrochloride, may be in any crystalline form and may prepared by any known method. For example, any one of the crystalline forms disclosed in US20020173645 may be used as a starting material.

In an embodiment, the crystalline raloxifene hydrochloride used in step a) is prepared by:

f) stirring raloxifene base and a C1-C3 alkanol, HCl and a polar solvent;
g) isolating a solid obtained from step f); and
h) drying the compound of step g).

In an embodiment, step f) is carried out at a temperature ranging from 0 to 40° C., typically for a period of time ranging from 30 minutes to 2 hours.

The C1-C3 alkanol used in step f) may be methanol, isopropanol or ethanol, preferably isopropanol.

The polar solvent may be tetrahydrofuran or dimethylformamide, preferably tetrahydrofuran.

The HCl may be added in the form of a solution in the polar solvent or in the form of a solution in the C1 to C3 alkanol or as a gas. Suitably, the C1 to C3 alkanol is isopropanol and the HCl is dissolved in the isopropanol.

The isolation in step g) may be carried out by filtering, decanting or centrifuging.

The drying in step h) is carried out at a temperature ranging from 30 to 80° C., typically for a period of time ranging from 2 to 15 hours.

According to another aspect of the present invention, there is provided crystalline raloxifene monohydrate prepared according to the present invention.

According to another aspect of the present invention, there is provided a pharmaceutical composition comprising crystalline raloxifene in hydrated form according to the present invention, and a pharmaceutically acceptable carrier.

The composition may be suitable for oral, rectal, transdermal, subcutaneous, intravenous, intramuscular or intranasal administration. Suitably, the composition is in the form of a tablet, a capsule, a gel, a suspension or a suppository. The composition may be formulated in a unit dosage form. Optionally, the dosage comprises the active ingredient in an amount ranging from 10 to 1000 mg, preferably in an amount ranging from 60 to 80 mg. The composition may be in the form of an aqueous suspension suitable for intravenous injection Alternatively, the composition is in the form of a tablet. In another alternative, the composition is in the form of a capsule. Suitably, the composition is in the form of a sustained release composition.

According to another aspect of the present invention, there is provided the use of crystalline raloxifene hydrochloride in hydrated form according to the present invention or a pharmaceutical composition according to the present invention in medicine.

According to yet another aspect of the present invention, there is provided the use of crystalline raloxifene hydrochloride in hydrated form according to the present invention or a pharmaceutical composition according to the present invention in the manufacture of a medicament for treating cancer, osteoporosis or in the manufacture of a medicament for inhibiting cartilage degradation.

According to a still further aspect of the present invention, there is provided a method of treating cancer or osteoporosis or of inhibiting cartilage, which method comprises administering to a patient in need thereof crystalline raloxifene in hydrated form according to the present invention, or a pharmaceutical composition according to the present invention.

Raloxifene hydrochloride hydrate, particularly raloxifene hydrochloride monohydrate, is a stable crystalline form of raloxifene hydrochloride, providing a stable formulation with pharmaceutically desirable characteristics. Raloxifene hydrochloride monohydrate is produced with high purity which makes it particularly suitable for pharmaceutical formulation. The process of the present invention is well suited for industrial scale-up.

DESCRIPTION OF ACCOMPANYING DRAWINGS

Figure 3:
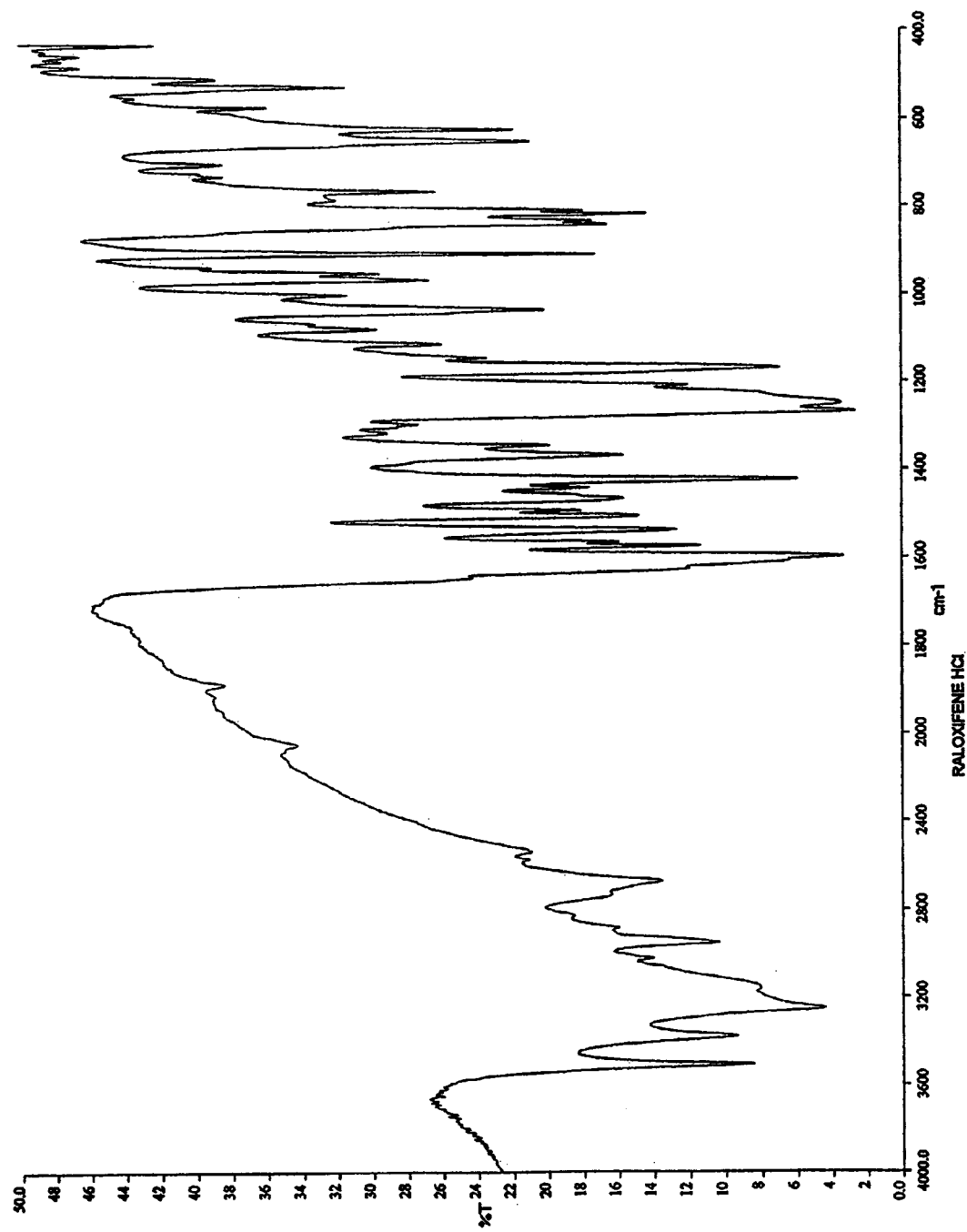

FIG. 3 shows a characteristic infrared absorption spectrum in potassium bromide of raloxifene hydrochloride monohydrate (which is prepared by example 2)
[Vertical axis: Transmission (%), Horizontal axis: Wave number $(cm^{-1})$]
The characteristic peaks for raloxifene hydrochloride monohydrate are indicated around 3506, 3378, 3251, 2952, 2669, 1572, 1490, 1438, 1366, 1143, 966, 816, 572, 526, 507 $cm^{-1}$.

DETAILED DESCRIPTION OF THE INVENTION

The present invention describes a crystalline polymorph of raloxifene hydrochloride in hydrated form preferably, a monohydrate form.

In one embodiment of the present invention, the process for the preparation of raloxifene hydrochloride in hydrated form is described. For some compounds, more than one hydrate may be isolated which differs only in respect of the number of water molecules incorporated per molecule of compound. In the present invention, it is understood that only water molecules are included in the compound, usually in a stiochiometric proportion.

The crystalline nature of polymorph raloxifene hydrochloride hydrate of the present invention can be characterized by its XRD, IR and DSC.

The X-ray powder diffraction pattern of crystalline polymorph of raloxifene hydrochloride monohydrate was measured on a Rigaku Dmax 2200 advanced X-ray powder diffractometer with a copper-K-α radiation source.

Figure 1:
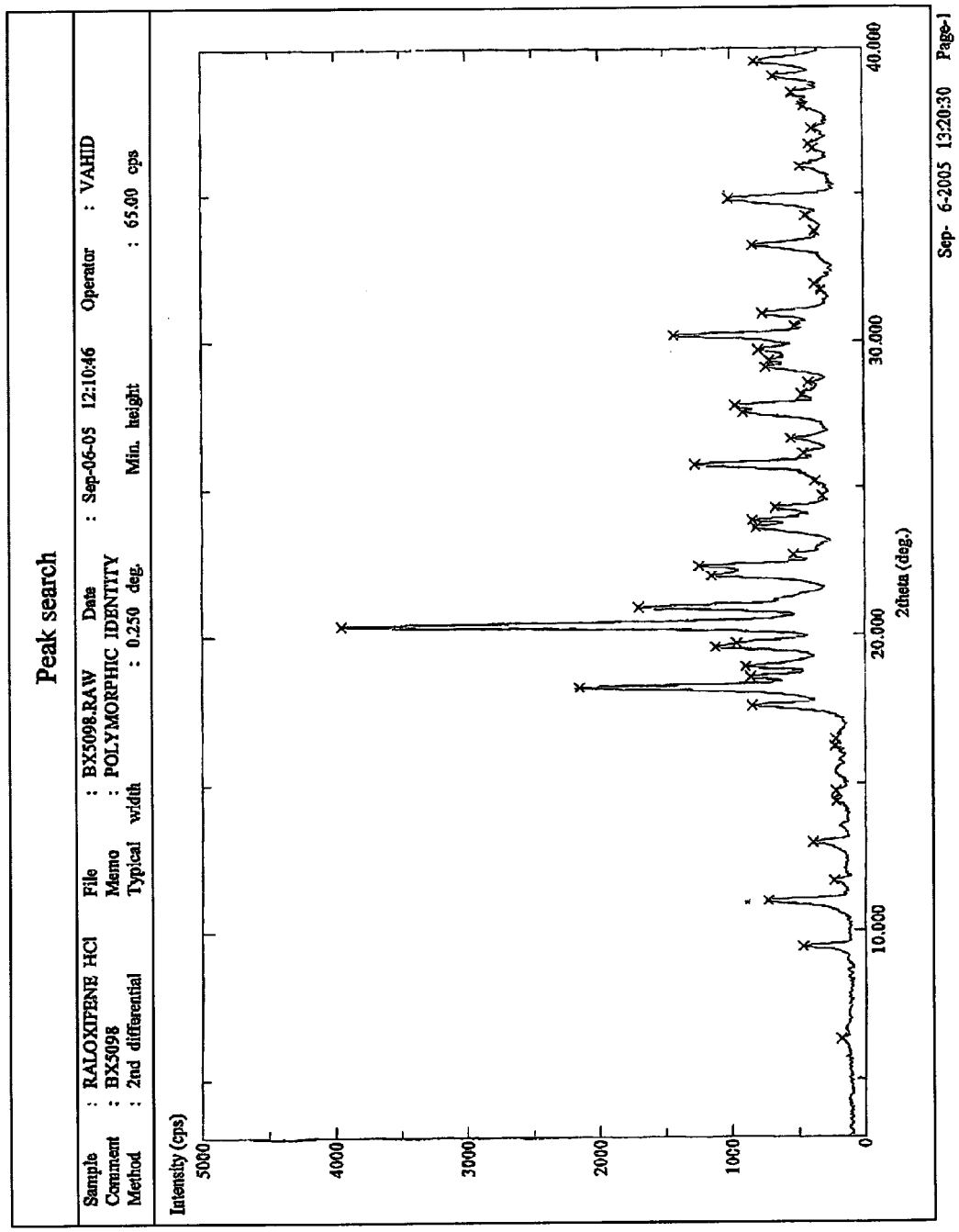
FIG. 1 shows a characteristic X-ray powder diffraction pattern of raloxifene hydrochloride monohydrate (which is prepared by example 2)
[Vertical axis: Intensity (cps), Horizontal axis: 2θ (degree)]

The crystalline polymorph of raloxifene hydrochloride monohydrate has an XRD pattern essentially as depicted in FIG. 1. The peaks are listed in Table 1. The X-ray powder diffraction pattern is expressed in terms of its °2θ values, intensity and relative intensity (%).

TABLE 1

| °2θ | Intensity | I/I$_0$ |
|---|---|---|
| 6.340 | 183 | 5 |
| 9.450 | 473 | 12 |
| 11.010 | 733 | 19 |
| 11.690 | 240 | 7 |
| 12.990 | 397 | 11 |
| 14.370 | 220 | 6 |
| 14.740 | 226 | 6 |
| 16.240 | 232 | 6 |
| 16.480 | 225 | 6 |
| 17.610 | 853 | 22 |
| 18.250 | 2154 | 55 |
| 18.580 | 861 | 22 |
| 18.920 | 899 | 23 |
| 19.580 | 1127 | 29 |
| 19.700 | 968 | 25 |
| 20.320 | 3955 | 100 |
| 20.920 | 1706 | 44 |
| 22.000 | 1153 | 30 |
| 22.330 | 1247 | 32 |
| 22.700 | 541 | 14 |
| 23.620 | 819 | 21 |
| 23.880 | 845 | 22 |
| 24.310 | 672 | 17 |
| 24.710 | 319 | 9 |
| 25.190 | 377 | 10 |
| 25.770 | 1275 | 33 |
| 26.140 | 462 | 12 |
| 26.640 | 552 | 14 |
| 27.520 | 913 | 24 |
| 27.760 | 971 | 25 |
| 28.130 | 469 | 12 |
| 28.550 | 422 | 11 |
| 29.100 | 740 | 19 |
| 29.350 | 712 | 18 |
| 29.690 | 794 | 21 |
| 30.180 | 1430 | 37 |
| 30.530 | 522 | 14 |
| 30.930 | 764 | 20 |
| 31.740 | 328 | 9 |
| 31.930 | 372 | 10 |
| 33.240 | 837 | 22 |
| 33.710 | 369 | 10 |
| 34.240 | 438 | 12 |
| 34.820 | 1013 | 26 |
| 35.920 | 480 | 13 |
| 36.550 | 381 | 10 |
| 36.700 | 411 | 11 |
| 37.250 | 387 | 10 |
| 38.020 | 450 | 12 |
| 38.480 | 537 | 14 |
| 39.040 | 675 | 18 |
| 39.560 | 816 | 21 |

Figure 2:
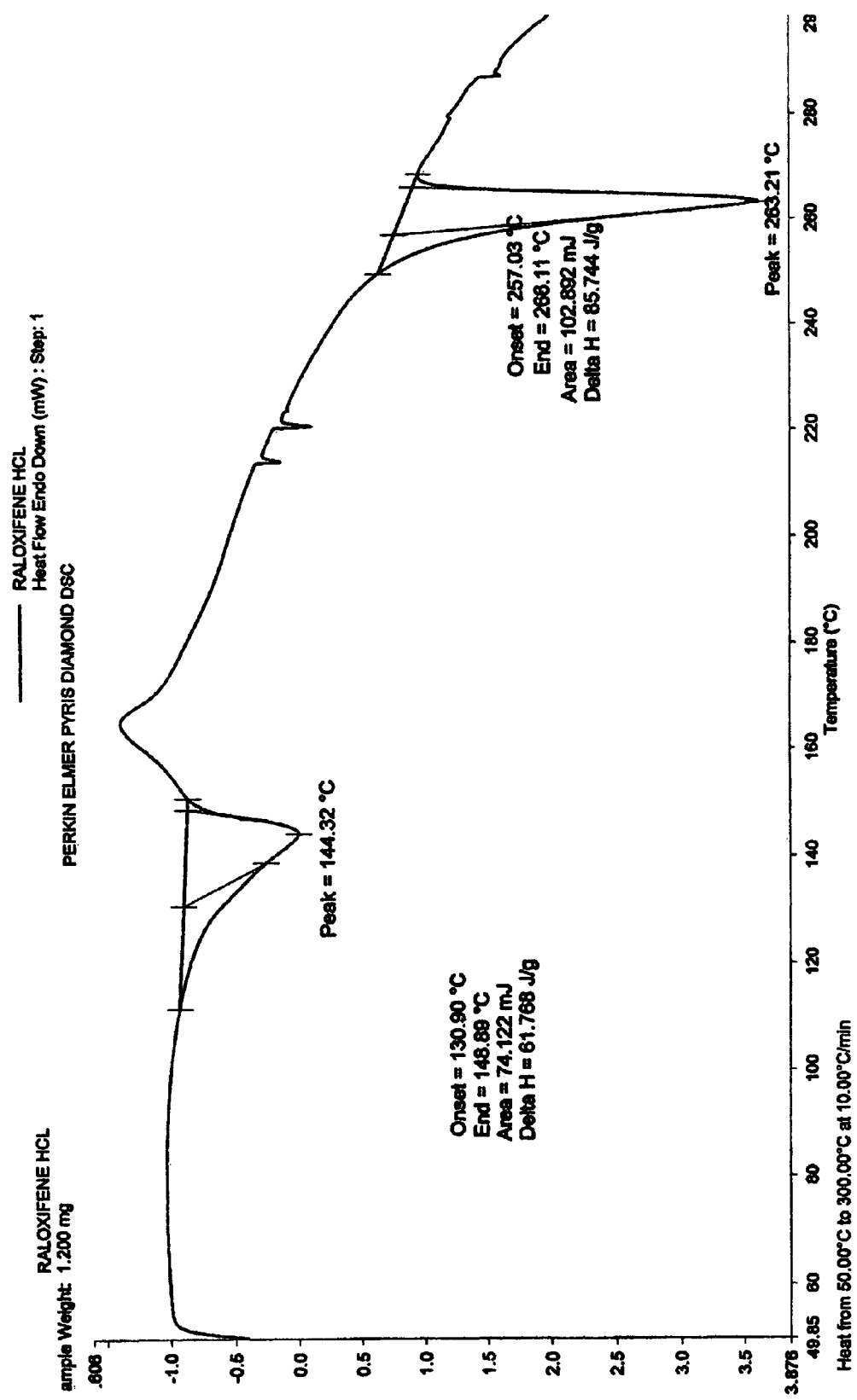
FIG. 2 shows a characteristic differential scanning calorimetric thermogram of raloxifene hydrochloride monohydrate (which is prepared by example 2)
[Vertical axis: Heat flow endo down (mW), Horizontal axis: Temperature (° C.)]
The differential scanning calorimetric thermogram exhibits a significant endo peaks at 144° C. and 263° C.

Raloxifene hydrochloride monohydrate of the present invention may also be characterized by DSC, exhibiting significant peaks at around 143° C. and 263° C. and as shown in FIG. 2.

The present invention further provides the IR data for crystalline raloxifene hydrochloride monohydrate which was measured by KBr-transmission method with identified the significant peaks at around 3506 cm$^{-1}$, 3378 cm$^{-1}$, 3251 cm$^{-1}$, 2952 cm$^{-1}$, 2669 cm$^{-1}$, 1572 cm$^{-1}$, 1490 cm$^{-1}$, 1438 cm$^{-1}$, 1366 cm$^{-1}$, 1143 cm$^{-1}$, 966 cm$^{-1}$, 816 cm$^{-1}$, 572 cm$^{-1}$, 526 cm$^{-1}$, 507 cm$^{-1}$ as shown in FIG. 3.

In an embodiment, the present invention provides a process for the preparation of raloxifene hydrochloride hydrate comprising the steps of:
a) stirring raloxifene base and a C1-C3 alkanol, HCl and a polar solvent at a temperature of 0-40° C. for 30 minutes to 2 hours;
b) isolating the solid obtained from step a) by filtering, decanting or centrifuging;
c) drying the compound of step b) at a temperature of 30-80° C. for 2 to 15 hours;
d) dissolving the compound in a C1-C4 alkanol or mixtures thereof, water and a water miscible solvent and optionally a colour removing agent at a temperature of 40-90° C. for 30 minutes to 2 hours;
e) charcoaling the solution for 1-2 hours;
f) filtering the above solution over hyflo;
g) adjusting the pH of the solution to acidic under stirring and cooling the reaction mass to 40° C.;
h) concentrating the reaction mass to 10-15% volume under vacuum;
i) isolating the solid obtained from step h), by filtering, decanting or centrifuging and
j) drying the compound at a temperature of 40-100° C. to afford the desired crystalline polymorph of raloxifene hydrochloride.

This embodiment of the process according to the present invention is particularly beneficial as raloxifene hydrochloride is easily crystallized from the solvent mixture, particularly when the solvent is a mixture of a C1-C3 alkanol and a polar solvent such as tetrahydrofuran or dimethylformamide. Preferably, the alkanol used in step a) is methanol, isopropyl alcohol or ethanol, more preferably, the alkanol is isopropanol. The polar solvent used in step a) is preferably tetrahydrofuran. The hydrochloric acid may be added in the form of a solution in the polar solvent or in the C1 to C3 alkanol or as a gas. Preferably, hydrochloride gas dissolved in isopropanol is added to the reaction mixture.

The crystallized raloxifene hydrochloride obtained in step c) is converted into its monohydrate without further purification and water is added to this solution.

The alkanol used in step d) may be selected from the group consisting of methanol, isopropyl alcohol, ethanol or butanol preferably, methanol.

The water miscible solvent is then added to this mixture which is selected from among dimethylormamide, dimethylacetamide, tetrahydrofuran or dimethylsulfoxide, preferably dimethylormamide.

Sodium metabisulphite, dry or in the form of an aqueous solution, may be added in step d) for better intensity of colour of the active pharmaceutical ingredient. Preferably, it is added as a dilute aqueous solution.

The resulting mixture is heated with stirring, preferably at about 60° C. The reaction mass is charcoalized and filtered. The solution in step g) is cooled to a temperature about 60-65° C. and adjusted to a pH ranging from 1.5 to 2.0 with an acid, such as hydrochloric acid. The hydrochloric acid may be added either in the form of an aqueous solution or as a gas; it is preferably added as an aqueous solution.

Preferably, the concentration of the reaction mass in step h) is carried out under a vacuum. The reaction mass may be partially distilled at about 11 volumes. Then the mixture is cooled to a temperature ranging from about 20-35° C. and the mixture is stirred in order to complete crystallization.

The resulting crystals are isolated by filtering or suction filtering of the solvent and washed with methanol. If desired, the washing step may be repeated. The product obtained is dried in vacuum or using hot air to achieve a water content of 3-4%.

The raloxifene base can be prepared by a variety of procedures well known in the prior art. The material to be employed as starting material, can be prepared by the procedure taught in U.S. Pat. No. 4,418,068 herein incorporated by reference in its entirety.

Raloxifene hydrochloride monohydrate is produced in substantially pure form. By "substantially pure" is meant a purity greater than or equal to 99.5%. Substantially pure raloxifene hydrochloride monohydrate forms another aspect of the present invention. Suitably, the substantially pure raloxifene hydrochloride monohydrate has a purity greater than 99.5%. Substantially pure raloxifene hydrochloride monohydrate according to the present invention may be used in the pharmaceutical compositions of the present invention and in the medical methods and uses of the present invention.

The present invention also provides a pharmaceutical composition comprising crystalline raloxifene in hydrated form, preferably as the monohydrate, and one or more pharmaceutically acceptable carriers, diluents or excipients therefor, the proportion and nature of which are determined by the chosen route of administration, and standard pharmaceutical practice. The pharmaceutical compositions or medicaments are prepared in a manner well known in the pharmaceutical art.

The hydrated raloxifene hydrochloride of the present invention, particularly the monohydrate, may be administered by a variety of routes including oral, rectal, transdermal, subcutaneous, intravenous, intramuscular and intranasal.

Depending on the method of administration, the composition for the treatment may be formulated as a tablet, a capsule for oral use, a gel or a suspension for transdermal delivery, a suppository or any other dosage form. Preferably, compositions are formulated in a unit dosage form, each dosage comprising the active ingredient in an amount ranging from 10-1000 mg, more usually 60-80 mg. The composition may be in the form of an aqueous suspension. For example, the composition may be an aqueous suspension that is suitable for intravenous injection. Alternatively, the composition may be in the form of a tablet or a capsule. Raloxifene hydrochloride hydrate may be formulated as a sustained release composition.

The carrier, diluent or excipient may be a solid, semi-solid, or liquid material, which can serve as a vehicle or medium for the active ingredient. Suitable carriers, diluents or excipients are well known in the art. The pharmaceutical compositions may be administered orally, for example, with an inert diluent or with an edible carrier. They may be enclosed in gelatin capsules or compressed into tablets. For the purpose of oral therapeutic administration, a hydrate, particularly a monohdyrate, according to the present invention may be incorporated with excipients and used in the form of tablets, capsules, elixirs, suspensions, syrups and the like.

The tablets, pills, capsules, and the like may also contain one or more of the following adjuvants: binders, such as microcrystalline cellulose, gum tragacanth or gelatin; excipients, such as starch or lactose; disintegrating agents such as alginic acid, corn starch and the like; lubricants, such as magnesium stearate; glidants, such as colloidal silicon dioxide; and sweetening agents, such as sucrose or saccharin.

When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives. Materials used in preparing these various compositions should be pharmaceutically pure and non-toxic in the amounts used.

For the purpose of parenteral administration hydrated raloxifene hydrochloride as provided by the present invention may be incorporated into a solution or suspension. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; and buffers such as acetates, citrates or phosphates. The parenteral preparation can be enclosed in ampoules, disposable syringes or multiple dose vials made of glass or plastic.

Raloxifene hydrochloride hydrate of the present invention may be used for treating a condition selected from the group consisting of cancer, osteoporosis or for inhibition of cartilage degradation.

The following examples are provided for the purposes of illustration and are not to be construed as limiting the scope of the claimed invention.

EXAMPLES

Example 1

Preparation of Raloxifene Hydrochloride

To 400 ml of tetrahydrofuan, 100 g of raloxifene base was charged and 150 ml of hydrogen chloride gas in isopropyl alcohol was added at 5-10° C. (over a time period of about 1 hour). The reaction mass was stirred at 25-30° C. for 15 minutes, heated to 30-35° C. and maintained for 1 hour. The reaction mass was cooled to 0-5° C. and maintained for 30 minutes. The material was filtered, washed with chilled tetrahydrofuran followed by chilled methanol and vacuum dried for 30 minutes. The material was further dried under vacuum initially at 40-45° C. for about 2 hours and then at 50-55° C. for 8 hours.

Example 2

Preparation of Raloxifene Hydrochloride Monohydrate

To dried raloxifene hydrochloride (of example 1), 700 ml of methanol, 300 ml of water, 10 ml of dimethyl formamide and sodium metabisulphite solution (0.5 g of sodium metabisulphite dissolved in 5 ml of water) was charged. The reaction mass was heated to reflux (67-72° C.) and maintained for 1 hour to obtain a clear solution. 5 g of activated charcoal was slurried in 30 ml of methanol, the contents were heated to reflux, maintained for 1 hour and filtered over hyflo and washed with 400 ml of a methanol:water mixture (1:1). The pH of the clear filtrate was adjusted to 1.50 to 2.00 using a 1:1 mixture of water and concentrated hydrochloric acid at 60-65° C. The reaction mass was concentrated to 1100 ml under vacuum. The reaction mass was cooled gradually to 25-30° C. under stirring and further stirred for 30 minutes. The obtained material was filtered, washed with 25 ml of methanol and vacuum dried. The material was further dried under vacuum at 80-85° C. to give raloxifene hydrochloride monohydrate.

Yield: 95 g.
HPLC purity: >99.5%
Melting point: 262° C.-265° C.
Water content (kf): 0.3-4%

The product was analyzed by X-ray diffraction analysis using Rigaku Dmax 2200 advanced X-ray powder diffractometer with a copper-K-α radiation source. The result is shown in FIG. 1 and is also listed numerically below.

The product was further analyzed using differential scanning calorimetry using a Perkin Elmer system. The differential scanning calorimetric chart is shown in FIG. 2.

The product was further analysed by Infrared Spectroscopy and the IR spectrum is shown in FIG. 3.

It will be appreciated that the invention may be modified within the scope of the appended claims.

The invention claimed is:

1. Crystalline hydrated raloxifene hydrochloride, having the formula

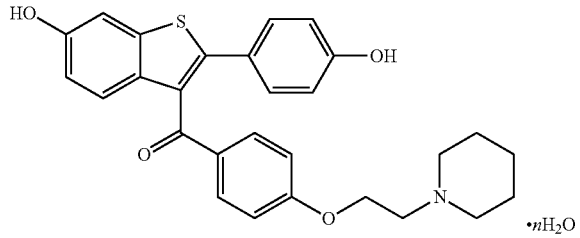

wherein n is an integer of 1 to 5, or a reciprocal of integers 2 to 5.

2. Crystalline hydrated raloxifene hydrochloride according to claim 1, wherein n is 1.

3. Crystalline raloxifene hydrochloride monohydrate according to claim 2, characterized by having an XRPD with peaks at 18.3 and 20.3° 2θ±0.2° 2θ.

4. Crystalline raloxifene hydrochloride monohydrate according to claim 3, characterized by having an XRPD with further peaks at 20.9, 22.0, 22.3, 25.8 and 30.2° 2θ±0.2° 2θ.

5. Crystalline raloxifene hydrochloride monohydrate according to claim 2, characterized by having an XRPD as shown in FIG. I.

6. Crystalline raloxifene hydrochloride monohydrate according to claim 2, characterized by having a differential scanning calorimetric thermogram exhibiting significant endo peaks at 144° C. and 263° C.

7. Crystalline raloxifene hydrochloride monohydrate according to claim 6, characterized by having a differential scanning calorimetric thermogram as shown in FIG. II.

8. Crystalline raloxifene hydrochloride monohydrate according to claim 2, characterized by having an infrared spectrum with peaks indicated around 3506, 3378, 3251, 2952, 2669, 1572, 1490, 1438, 1366, 1143, 966, 816, 572, 526 and 507 cm$^{-1}$.

9. Crystalline raloxifene hydrochloride monohydrate according to claim 8, characterized by having an infrared spectrum as shown in FIG. III.

10. Crystalline raloxifene hydrochloride monohydrate according to claim 2, having a water content ranging from 3 to 4%.

11. A process for the preparation of crystalline raloxifene hydrochloride monohydrate of claim 2 comprising the steps of:
    a) dissolving crystalline raloxifene hydrochloride in a C1-C4 alkanol or mixtures thereof, water and a water miscible solvent and optionally a colour removing agent;
    b) optionally charcoaling and filtering the solution;
    c) adjusting the pH of the solution to acidic;
    d) isolating the solid obtained from step c); and
    e) drying the compound to afford the crystalline polymorph of raloxifene hydrochloride monohydrate.

12. The process according to claim 11, wherein the crystalline raloxifene hydrochloride used in step a) is prepared by:
    f) stirring raloxifene base and a C1-C3 alkanol, HCl and a polar solvent;
    g) isolating a solid obtained from step f); and
    h) drying the compound of step g).

13. Crystalline raloxifene hydrochloride monohydrate prepared according to claim 11.

14. A pharmaceutical composition comprising crystalline raloxifene in hydrated form according to claim 1, and a pharmaceutically acceptable carrier.

15. The pharmaceutical composition according to claim 14, wherein the composition is suitable for oral, rectal, transdermal, subcutaneous, intravenous, intramuscular or intranasal administration.

16. The pharmaceutical composition according to claim 14, wherein the composition is formulated in a unit dosage form.

17. A method of treating cancer or osteoporosis or of inhibiting cartilage degradation, which method comprises administering to a patient in need thereof crystalline raloxifene in hydrated form according to claim 1, or a pharmaceutical composition comprising the crystalline raloxifene hydrochloride in hydrated form.

* * * * *

UNITED STATES PATENT AND TRADEMARK OFFICE
CERTIFICATE OF CORRECTION

PATENT NO. : 8,344,149 B2  Page 1 of 1
APPLICATION NO. : 12/445385
DATED : January 1, 2013
INVENTOR(S) : Pathi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 925 days.

Signed and Sealed this
First Day of September, 2015

Michelle K. Lee
*Director of the United States Patent and Trademark Office*